US008642316B2

(12) United States Patent
Carboulec

(10) Patent No.: US 8,642,316 B2
(45) Date of Patent: Feb. 4, 2014

(54) LEPTOSPIROSIS CULTURE PROCESS

(75) Inventor: Nicolas Pierre Yves Carboulec, Lyons (FR)

(73) Assignee: Merial Limited, Duluth, GA (US)

( * ) Notice: Subject to any disclaimer, the term of this patent is extended or adjusted under 35 U.S.C. 154(b) by 1761 days.

(21) Appl. No.: 11/404,690

(22) Filed: Apr. 14, 2006

(65) Prior Publication Data

US 2007/0031456 A1 Feb. 8, 2007

Related U.S. Application Data

(60) Provisional application No. 60/673,227, filed on Apr. 20, 2005.

(51) Int. Cl.
*C12N 1/38* (2006.01)
*C12N 1/36* (2006.01)
*C12N 1/00* (2006.01)

(52) U.S. Cl.
USPC ............................ 435/244; 435/243; 435/245

(58) Field of Classification Search
USPC .................................................. 435/243–245
See application file for complete search history.

(56) References Cited

U.S. PATENT DOCUMENTS 3,816,261 A 6/1974 Torney
4,133,717 A 1/1979 Johnson et al.

OTHER PUBLICATIONS

Breed et al "The Effect of Temperature on the Continuous Ferrous-iron Oxidation Kinetics of a Predominantly *Leptospirillum ferrooxidans* Culture" Biotechnology and Bioengineering, vol. 65, No. 1, Oct. 5, 1999, p. 44-53.*

Stalheim "Leptospiral Selection, Growth, and Virulence in Synthetic Medium" Journal OP Bacteriology. 1966 vol. 92, No. 4, p. 946-951.*

G. Z. Khisamov "Fatty Acids as Resource of Carbon for *Leptospirae*" J. Hygien Epidemiology Microbiology, 32, 1988 No. 1, p. 87-93.*

Johnson et al. "Nutrition of *Leptospira pomona* II. Fatty Acid Requirements" J. Bacteriol, May 1963 85(5) 976-982.*

Shenberg "Growth of Pathogenic *Leptospira* in Chemically Defined Media" Journal of Bacteriology, 93(5) May 1967, 1598-1606.*

Staneck, Joseph L: et al., Growth Requirements of Pathogenic *Leptospira*, Infection and Immunity, Jun. 1973, 7(6): 886-897.

Khisamov G., et al., Fatty Acids as Resource of Carbon for *Leptospirae*, Journal of Hygiene Epidemiology Microbiology and Immunology, vol. 32, No. 1 (1989) pp. 87-93.

Bey R., et al., Protein-Free and Low Protein Media for the Cultivation of *Leptospira*, Infection and Immunity, vol. 19, No. 2 (1978) pp. 562-569.

* cited by examiner

*Primary Examiner* — Thane Underdahl
(74) *Attorney, Agent, or Firm* — Judy Jarecki-Black; Ruoying Chen; Merial Limited

(57) ABSTRACT

A process for the culture of Leptospires in a protein-free culture medium and without any fatty acid source in the culture medium, wherein a fatty acid source is fed continuously or intermittently.

4 Claims, No Drawings

LEPTOSPIROSIS CULTURE PROCESS

RELATED APPLICATIONS

This application claims priority to Provisional U.S. Application Ser. No. 60/673,227 filed Apr. 20, 2005, the contents of which are hereby expressly incorporated herein by reference.

INCORPORATION BY REFERENCE

All documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention

FIELD OF THE INVENTION

The invention provides a process for the culture of Leptospires, which reduces the use of serum protein or serum albumin in the culture medium. The present invention provides also a process for the adaptation of leptospires to grow in a protein-free culture medium. The present invention encompasses also these adapted leptospires, their use in culture process, and immunogenic compositions and vaccine compositions.

BACKGROUND OF THE INVENTION

A number of pathogenic leptospires are known to be of economic importance because they cause disease in different animal species, for example, in dogs, cattle, pigs, sheep and horses. Notably, it is a common cause of abortion, stillbirth, and neonatal mortality in swine, of renal and hepatic disease in dogs. To prevent such disease, vaccines consisting of killed bacteria have been prepared from cultures of leptospires.

Leptospires are bacteria, including various serovars, and of these *canicola, icterohaemorrhagiae, pomona, grippotyphosa, bratislava, australis, ballum, aulumnalis* and *hardjo* are most frequently responsible for leptospirosis of animals and humans.

Leptospires are most often cultivated in protein-containing media. These media contain serum from various species, notably from rabbit, bovine, equine . . . . To prepare such vaccines, it would be desirable to have a high density of the leptospires in the culture medium and/or to achieve this high density by concentration procedure. After administration of a vaccine comprising such serum components, adverse reactions may occur. The risk of adverse systemic reactions is increased due to the concentration of the heterologous serum proteins, in particular serum albumin. The adverse systemic reactions include anaphylaxis, hypersensitivity and atypical reactions such as vomiting and diarrhea.

Various chemically defined protein-free media for the growth of leptospires have been proposed. In order to obtain the desired rapid and abundant growth of organisms necessary for the efficient production of vaccines, it has been necessary to supplement such media with a source of fatty acids, notably Tween®, metabolisable by leptospires. But the source of fatty acid may also be toxic for leptospires, so to reduce this disadvantage serum from animal origin or serum albumin was added to the culture media.

Fatty acids are the major carbon and energy source for leptospires (Bey R. F. and Johnson R. C., Infection and Immunity, 1978, 19(2), 562-569). In addition, long-chain fatty acids are essential nutrients because the leptospires are unable to synthesize these acids de novo. Although they can decrease the length of the carbon chain of fatty acids and they can desaturate fatty acids, the leptospires can not increase the length of these compounds. Because free fatty acids are toxic to the leptospires, serum or serum albumin is incorporated into culture media to bind the fatty acids in an available but nontoxic form. Media containing bovine serum albumin (BSA) and Tween® have most commonly been accepted among the manufacturers to produce Leptospires vaccines. Ellinghausen and McCullough (American Journal of Veterinary Research, 1965, 26(1), 39-44) have shown that Leptospires may be grown on a serum-free medium, provided a complex of albumin and lipid is supplied. These workers further (Ellinghausen and McCullough, American Journal of Veterinary Research, 1965, 26(1), 45-51) showed that Tween® 80 could serve as a lipid source for *Leptospira pomona* but that excess lipid (more than 0.1% of Tween® 80) caused a lysis of the leptospires and a falloff in their growth.

Vaccine production requires the use of large volumes of culture media, and the most expensive component is animal serum or serum albumin. The serum proteins are also the cause of adverse systemic vaccine reactions.

To reduce the systemic reactions, one can purify vaccines to remove components thereof which cause the systemic reactions. Animal vaccine preparations can typically be purified by conventional methods such as filtration, diafiltration or centrifugation to remove the supernatant. Other methods of purification that yield highly purified antigens are seldom employed because they are cost prohibitive in the preparation of animal vaccines. At any rate, these purification methods were not effective for removing albumin from vaccines or precursors thereof.

To circumvent the disadvantages of adverse systemic reactions and of the use of animal serum or serum albumin, a number of chemically defined media for the cultivation of leptospires have been proposed in the prior art.

Anion-exchange resins also binds fatty acids, and they can be used as a substitute for albumin for the cultivation of leptospires. The major disadvantage of using the resins in this manner is that they must be separated from the leptospires when they are harvested (Bey R. F. and Johnson R. C., Infection and Immunity, 1978, 19(2), 562-569).

In these attempts, Tween® (ethoxylated fatty acid ester of sorbitan, polysorbate) was usually employed as a fatty acid source in the metabolism of leptospires since the microorganism utilizes long-chain fatty acids. However, commercial Tween® is usually contaminated with unesterified fatty acids, polyethylene glycols and other by-products, and these materials impede the growth of leptospires. Hence removal of the contaminants from commercial Tween® by such methods as ion exchange resin treatment, charcoal-treatment and polyvinylpyrrolidone-treatment, was attempted.

Staneck et al. (Staneck et al., Infect. Immun., 1973, 7(6), 886-897) reported that albumin was not necessary for cultivation of *L. canicola* and *L. Pomona* if the Tween® 80 (polyoxyethylene sorbitan monooleate) was passed through an anion-exchange column to reduce its free-fatty acid content. However the attempts of Bey & Johnson to detoxify the Tween® by passage through an anion-exchange column were unsuccessful (Bey R. F. and Johnson R. C., Infection and Immunity, 1978, 19(2), 562-569).

Bey & Johnson reported the growth of leptospires in a synthetic medium containing charcoal treated Tween® (Bey R. F. and Johnson R. C., Infection and Immunity, 1978, 19(2), 562-569).

Polyvinylpyrrolidone (PVP)-treated Tween® was used to prepare a protein-free medium for cultivation of leptospires (Schönberg A., Zbl. Bakt. Hyg., 1983, 254, 540-544). PVP is a synthetic colloid showing a behaviour similar to that of serum protein. However some serovars of leptospires, notably *L. grippotyphosa*, did not grow in this medium.

Kojima et al. (Kojima et al., Microbiol. Immunol., 1984, 28(8), 949-954) reported the growth of leptospires in a synthetic medium containing detoxified Tween®. The detoxification was done by extraction of unesterified fatty acids with n-hexane.

The removal of the Tween® contaminant or the detoxification of Tween® was not easy. Notably due to the great variation of composition of the commercial Tween®, from supplier to another one and from lot to lot, these methods could be incomplete. More than that, these methods were time consuming and expensive.

Some experiments were attempt to grow leptospires directly in a protein-free medium and with untreated Tween®. Stalheim (Stalheim O. H. V., J. Bacteriol., 1966, 92(4), 946-951) wanted to grow leptospires in a medium without protein, notably without albumin and without any detoxifying agent, but with untreated Tween® as fatty acid source. Face to culture problem, Stalheim proposed to adapt these leptospires to survive and consume untreated Tween® by successive passages on culture media containing an increased concentration of untreated Tween® at each passage. After several subcultures, as long as 7 to 27 days per subculture, *Leptospira pomona* tolerated higher concentrations of Tween® 80 (0.06%). But a concentration of 0.1% of Tween® 80 was extremely lytic for Leptospires. With 0.06% of Tween® 80, the final biomass of Leptospires was only 2.0 10e8 bacteria/ml, which is inferior to the biomass obtained with classical culture method using treated Tween®, notably charcoal-treated Tween® 80, e.g. *Leptospira canicola* with 5 10e8 bacteria/ml or *Leptospira icterohaemorrhagiae* with 8.4 10e8 bacteria/ml (Bey and Johnson, supra).

So there is still a need for a better culture process for leptospires.

One objective of the invention is to provide an adaptation process of Leptospires to grow in a protein-free culture medium. A second objective of the present invention is to provide a new process for the large scale culture of Leptospires in a protein-free culture medium.

SUMMARY OF THE INVENTION

A first embodiment of the present invention is a process for the culture of Leptospires in a protein-free culture medium and without any fatty acid source in the culture medium, wherein a fatty acid source is fed continuously or intermittently in such a way that the specific growth rate ($\mu$) of Leptospires is inferior to its maximum growth rate ($\mu max$).

A second embodiment of the present invention is a process for the culture of Leptospires at a constant volume comprising: (a) a continuous feeding of an input medium and a continuous removal of the culture, (b) a culture medium comprising a detoxifying agent and a fatty acid source, (c) when Leptopsira growth starts, the input medium is fed in order to obtain a dilution rate of the culture inferior to the maximum growth rate ($\mu max$) of Leptospires; (d) the input medium comprising a concentration of the fatty acid source inferior to the one of the culture medium; the fatty acid source being then the growth-limiting nutrient; and (e) decreasing the concentration of the detoxifying agent in the culture medium such as the Leptospires obtained by this process are able to grow in a protein-free medium without any detoxifying agent.

A further embodiment of the present invention is to grow the leptospires obtained by the process according to the first or the second embodiment of the present invention in a subculture in a protein-free culture medium without any detoxifying agent.

Another embodiment of the invention is a process for the adaptation of leptospires to grow in a protein-free culture medium using a culture process according to the present invention.

A further embodiment of the present invention is the leptospires adapted to grow in a protein-free culture medium by the process of the invention.

Another embodiment of the present invention is the use of the adapted leptospires to grow in a subculture in a protein-free culture medium comprising a fatty acid source and without any detoxifying agent.

A further embodiment of the present invention is the immunogenic compositions or vaccine compositions containing, as immunogen, such leptospires and a veterinary acceptable diluent or carrier.

It is noted that in this disclosure and particularly in the claims, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DETAILED DESCRIPTION OF THE INVENTION

For the culture of bacteria, notably of Leptospires, various culture processes may be used.

In a batch culture process, proliferation of the bacteria stops at some point of the culture period mainly due to the exhaustion of nutrients. In order to improve this simple batch culture process, a so-called fed-batch culture process is carried out in which exhausted nutrients, for example sugars, amino acids or fatty acids, are added continuously or intermittently during the culture period.

In this specification, a "batch culture process" means a process which comprises inoculating bacteria into a medium in a culture vessel, and carrying out the culture without substantial addition of part or all of the nutrients or a new medium until the end of the culture, and a "fed-batch culture process" means a process comprising inoculating bacteria into a medium in a culture vessel, and carrying out the culture while adding part or all of the nutrients or a fresh medium (feed) continuously or intermittently into the culture vessel, without substantially taking out the culture fluid from the culture vessel.

A chemostat culture process means a process which allows to maintain an exponential bacterial growth during a long period of time with a constant bacterial concentration having a controlled growth rate (about chemostat, see Yee and Blanch, Biotechnol. Bioengineer., 1993, 41, 221-230; Dauner et al., J. Bacteriol., 2001, 183(24), 7308-7317).

The growth rate (μ) is the ratio of ln 2 (natural logarithm) divided by the doubling-time of the bacteria, expressed in hours. This doubling-time depends on the culture conditions, such as temperature, pH, water activity, pressure . . . . The maximum growth rate (μmax) corresponds to the shorter doubling-time for given culture conditions, for which the substrates (carbon source, fatty acid source, nitrogen source . . . ) are not limiting the bacterial growth.

Incorporated into culture media for Leptospires, detoxifying agents are able to bind the free fatty acids in an available but nontoxic form. Some examples of detoxifying agents are albumin, anion-exchange resins. In another way, a detoxification treatment of the fatty acid source may be done before the incorporation of the fatty acid source into the culture media. Some examples of these treatments are ion exchange resin treatment, charcoal-treatment and polyvinylpyrrolidone-treatment. In contrario, untreated fatty acid sources (e.g. untreated Tween®) are not detoxified.

A protein-free medium is a medium without any protein or polypeptide or peptide.

The adaptation process is a culture growing at a controlled growth rate in a controlled environment: concentration of fatty acid source in the culture medium close or equal to zero throughout the process, absence or minute amount of the detoxifying agent in the culture medium from the beginning of the culture for a fed-batch or at the end of the culture for a chemostat. In fed-batch, residual quantity of detoxifying agents may be carry-over by the inoculum in the culture, depending upon the conditions of inoculation. The resulting bacterial population from the adaptation process can grow in a medium containing all the needed substrates without any detoxifying agent.

The present invention concerns a process for the culture and adaptation of Leptospires in a protein-free culture medium and without any fatty acid source in the culture medium, wherein a fatty acid source is fed continuously or intermittently in such a way that the specific growth rate (μ) of Leptospires is inferior to its maximum growth rate (μmax).

In one embodiment, the process is a fed-batch culture for the adaptation of leptospires.

One particular advantage of the fed-batch culture process is the control of the growth rate of the culture in the vessel, compared to batch culture process. By using one essential nutrient in the feed and by defining the feed rate evolution with time, it is then possible to obtain a specific growth rate. For example, a growth rate which does not cause the formation of acetic acid has been obtained for fed-batch culture of *Escherichia coli* (Korz et al., J. Biotechnol., 1995, 39(1), 59-65).

The present invention provides a process which comprises culturing leptospires in a suspension fed-batch culture stably for a long period at a specific growth rate inferior to the maximum growth rate (μmax) of Leptospires.

The fed-batch culture process comprises (a) Introduction of a protein-free culture medium into a fermenter, wherein this culture medium does not comprise any fatty acid source and any detoxifying agent;

(b) Inoculation of this culture medium with a Leptospires strain culture;

(c) Feeding the culture with a nutrient solution at a feed rate such as the specific growth rate (μ) is inferior to the maximum growth rate (μmax) of Leptospires strain, the nutrient solution containing the fatty acid source;

(d) Continuing the culture until a substantial increase of the Leptospires biomass or at the end of the Leptospires growth;

(e) Harvesting of the Leptospires biomass.

The specific growth rate (μ) is inferior to the maximum growth rate (μmax) of leptospires. The specific growth rate (μ) may be constant or not. The specific growth rate (μ) is advantageously inferior to 0.045 $h^{-1}$, in particular inferior or equal to 0.03 $h^{-1}$, more particularly inferior or equal to 0.025 $h^{-1}$. The determination of the maximum growth rate of a Leptospires strain is further described in example 1.

The culture medium present inside the fed-batch vessel and the nutrient solution feeding during the fed-batch culture do not contain serum protein or serum albumin. They are protein-free.

The culture medium for the fed-batch may be the JH medium without albumin and without Tween® (Johnson and Harris, J. Bacteriol., 1967, 14(1), 27-31).

Advantageously, the culture medium for the fed-batch process comprises: Na2HPO4, KH2PO4, NaCl, NH4Cl, glycerol, CaCl2, MgCl2, ZnSO4, FeSO4, CuSO4, cyanocobalamin (vitamin B12), thiamine HCl (vitamin B1).

In the culture medium of the fed-batch process of the present invention, detoxifying agents do not need to be added as done in prior art (e.g. addition of albumin or anion-exchange resins).

The nutrient solution for the fed-batch process comprises a source of fatty acids.

The fatty acid source is notably sodium salts of fatty acids, fatty acids emulsions, ethoxylated fatty acids, esterified fatty acids, for example esters of sorbitan, sorbitol, polyglycerol, polyethyleneglycol, and fatty acids, and preferably Tween® 80, Tween® 60, Tween® 40, Tween® 20, Tween® 85. These fatty acids are selected having a carbon chain from 12 to 18 residues (C12 to C18). These Tween® are used in the present invention untreated. It may be also possible to use treated-Tween®, in particular charcoal-treated, PVP-treated, or ion exchange resins treatments.

In a particular embodiment of the fed-batch process of the present invention, the nutrient solution comprises Tween® which does not need to be treated, notably detoxified as done in prior art (e.g. charcoal-treated, PVP-treated, passage through a column containing a ion exchange resin).

The inoculation of the culture medium with a Leptospires strain is done with an inoculum from 1.0 10e8 to 5.0 10e9, and preferably about 0.8 10e9 bacteria/ml. The inoculum volume represents from 1% to 20% volume/volume (v/v) of the culture volume, and preferably 5% to 10%.

The culture temperature is chosen between +27° C. and +37° C. Preferably, the culture temperature is +29° C.

The pH value of the culture medium is maintained in the range of 6.8 to 7.6.

Preferably, the pH value of the culture medium is about 7.2.

Leptospires are obligate aerobes. So aeration of the culture must be done, e.g. by addition of pure oxygen gas.

The biomass concentration of the leptospires according to the fed-batch culture process of the present invention reached at least 5.0 10e8 bacteria/ml, advantageously at least 1.0 10e9 bacteria/ml and more advantageously at least 2.0 10e9 bacteria/ml. The fed-batch culture time is comprised between 60 hours and 200 hours, in particular between 90 hours and 120 hours.

With the fed-batch culture process of the invention, the adaptation of the leptospires was done in only one passage, corresponding to about 3-8 generations of leptospires.

For leptospires in a culture medium without any detoxifying agent, the untreated Tween® toxicity threshold is 0.002% before any adaptation of the Leptospires strain, and is 0.06% after selection (Stalheim O. H. V., J. Bacteriol., 1966, 92(4), 946-951).

With the fed-batch adaptation processes according to the present invention, Leptospires strains are advantageously adapted in only one passage to grow in a protein-free culture medium without any detoxifying agent, notably without albumin. The adapted strains were able to grow in a protein-free culture medium without any detoxifying agent, and with high concentration of untreated Tween®, which are known in the prior art to be lytic in adaptation processes (Stalheim, supra). In particular, the high concentration of untreated Tween® may be at least 1.25 g/l, more particularly at least 2.5 g/l.

A second aspect of the present invention is a chemostat culture of Leptospires at a constant volume comprising: (a) a continuous feeding of an input medium and a continuous removal of the culture medium, (b) a culture medium comprising a detoxifying agent and a fatty acid source, (c) when Leptopsira growth has started, the input medium is fed in order to obtain a dilution rate of the culture inferior to the maximum growth rate (μmax) of Leptospires; (d) the input medium comprising a concentration of the fatty acid source inferior to the one of the culture medium; the fatty acid source being then the growth-limiting nutrient; and (e) decreasing the concentration of the detoxifying agent in the culture medium throughout the culture such as the Leptospires obtained by this process are able to grow in a protein-free medium without any detoxifying agent.

In a particular embodiment, the chemostat culture of Leptospires at a constant volume comprises: (a) a continuous feeding of an input medium and a continuous removal of the culture medium, (b) a culture medium comprising a detoxifying agent and a fatty acid source, (c) when Leptopsira growth has started, the input medium is fed in order to obtain a dilution rate of the culture inferior to the maximum growth rate (μmax) of Leptospires; (d) the input medium comprising a concentration of the fatty acid source inferior to the one of the culture medium; the fatty acid source being then the growth-limiting nutrient; and (e) the input medium with decreasing concentrations of the detoxifying agent throughout the culture such as the Leptospires obtained by this process are able to grow in a protein-free medium without any detoxifying agent.

The specific growth rate (μ) is advantageously inferior to 0.045 $h^{-1}$, in particular inferior or equal to 0.03 $h^{-1}$, more particularly inferior or equal to 0.025 $h^{-1}$. The determination of the maximum growth rate of a Leptospires strain is further described in example 1.

The culture medium for the chemostat may be the JH medium (Johnson and Harris, J. Bacteriol., 1967, 14(1), 27-31).

Advantageously, the culture medium for the chemostat process comprises: Na2HPO4, KH2PO4, NaCl, NH4Cl, glycerol, CaCl2, MgCl2, ZnSO4, FeSO4, CuSO4, cyanocobalamin (vitamin B12), thiamine HCl (vitamin B1), Tween® 80 and fraction V of BSA.

The concentration of albumin may be between about 0.5% w/v and about 1% w/v (weight/volume), preferably 1% w/v. The concentration of Tween® may be between about 0.1% w/v and 0.35% w/v.

An input medium is fed into the chemostat at a dilution rate inferior to the maximum growth rate of the Leptospires strain. The input medium comprises with an albumin concentration decreasing down to zero.

The inoculation of the culture medium into the chemostat with a Leptospires strain is done with an inoculum from 1.0 10e8 to 5.0 10e9, and preferably about 0.8 10e9 bacteria/ml. The inoculum volume represents from 1% to 20% volume/volume (v/v) of the culture volume, and preferably 5% to 10% v/v.

The culture temperature, the pH value and the aeration of the culture are done as previously described for fed-batch culture.

With the chemostat culture process of the invention, the adaptation of the leptospires is done in about 100 generations of leptospires, in particular in about 40 generations.

Contrary to the prior culture process with albumin, the culture processes of the present invention do not need a step to purify the final product in order to eliminate the albumin. Generally this step is a protein exclusion. This may result in a difference of protein composition that could be observed in the protein profiles obtained after SDS-PAGE (sodium dodecyl sulphate-polyacrylamide gel electrophoresis); a break in the protein profile is only observed after protein exclusion used to eliminate albumin in prior culture processes.

The leptospires obtained by ever the fed-batch or chemostat processes of the invention can be used for one or several serial subcultures in a protein-free culture medium without any detoxifying agent and with a fatty acid source, preferably an untreated Tween®.

In one embodiment, the subculture is done with a specific growth rate (μ) inferior to the maximum growth rate (μmax) of Leptospires. In particular, the subculture is a fed-batch culture.

In another embodiment, the subculture is done with a specific growth rate (μ) equal to the maximum growth rate (μmax) of Leptospires. In particular, the subculture is a batch culture.

In a particular embodiment, the adapted leptospires according to the present invention can grown further into batch fermenters and in protein-free culture media without any detoxifying agent, notably without albumin, and with a fatty acid source.

These protein-free culture media may be those described as culture medium for the fed-batch culture process, but added with a fatty acid source, as previously described.

In another embodiment, the adapted leptospires according to the present invention can be grown further into batch fermenters and in protein-free culture media without any detoxifying agent, notably without albumin, and with untreated Tween®, which may be present at high concentration. In particular, the high concentration of untreated Tween® may be at least 1.25 g/l, more particularly at least 2.5 g/l.

The biomass concentration of the adapted leptospires according to our invention reached at least 5.0 10e8 bacteria/ml, in particular 1.0 10e9 bacteria/ml, advantageously at least 2.0 10e9 bacteria/ml and more advantageously at least 4.0 10e9 bacteria/ml.

The present invention encompasses the leptospires adapted to grow in a protein-free culture medium by the processes according to the present invention. The present invention encompasses also the adapted leptospires obtained after one or several serial subcultures according to the present invention.

Leptospires are inactivated in particular with merthiolate (e.g. Thimerosal®, Sigma Chemical Co. St Louis, Mo. USA) or formaldehyde or NaCl, ethyleneimine or derivatives thereof (binary ethyleneimine), beta-propiolactone. After inactivation, leptospires are suspended in a veterinary acceptable diluent or carrier, notably in sterile water, to form inactivated immunogenic compositions or vaccine compositions.

The present invention comprises also immunogenic compositions or vaccine compositions containing, as immunogen, leptospires adapted, by a process according to the invention, to grow in a protein-free culture medium without any detoxifying agent and inactivated and a veterinary acceptable diluent or carrier.

The present invention comprises also immunogenic compositions or vaccine compositions containing, as immunogen, leptospires grown by a subculture according to the present invention and inactivated and a veterinary acceptable diluent or carrier.

Optionally, at least one adjuvant may be added to the leptospire suspension obtained after culture according to the present invention or to the immunogenic compositions or vaccine compositions of the present invention. Suitable adjuvants include aluminium hydroxide, aluminium phosphate, aluminium oxide, block copolymers such as Pluronic®, acrylic or methacrylic acid polymers, preferably carbomers such as Carbopol®, anhydride maleic and alkenyl copolymers such as EMA®, oil-emulsions, saponins, QuilA, and their combinations, such as combinations of aluminum hydroxide and saponin.

The oil-emulsion may notably be an oil-in-water emulsion, in particular the emulsion SPT described p 147 "Vaccine Design, The Subunit and Adjuvant Approach" edited by M. Powell, M. Newman, Plenum Press 1995, and the emulsion MF59 described p 183 in the same book. The oil-in-water emulsion may in particular be based on light liquid paraffin oil (European Pharmacopeia type, e.g. of Drakeol®, Bayol F® or Marcol 52®); isoprenoid oil such as squalane, squalene; oil resulting from the oligomerization of alkenes, in particular of isobutene or of decene; esters of acids or alcohols containing a linear alkyl group, more particularly vegetable oils, ethyl oleate, propylene glycol di(caprylate/caprate), glyceryl tri(caprylate/caprate), propylene glycol dioleate; esters of branched fatty alcohols or acids, in particular esters of isostearic acid. The oil is used in combination with emulsifiers to form the emulsion. The emulsifiers are preferably nonionic surfactants, in particular the esters of sorbitan, mannide, glycerol, polyglycerol, propylene glycol and of oleic, isostearic, ricinoleic or hydroxystearic acid, which are optionally ethoxylated, the polyoxypropylene-polyoxyethylene block copolymers, in particular the Pluronic® copolymers, especially L121.

The acrylic or methacrylic acid polymers and the anhydride maleic and alkenyl copolymers constitute a same adjuvant family which are formed of basic units of the following formula:

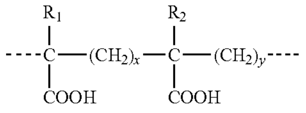

in which:

$R_1$ and $R_2$, which are identical or different, represent H or $CH_3$ x=0 or 1, preferably x=1 y=1 or 2, with x+y=2

For the anhydride maleic and alkenyl copolymers, x=0 and y=2. For the acrylic or methacrylic acid polymers, x=y=1.

The polymers of acrylic or methacrylic acid are preferably crosslinked, in particular with polyalkenyl ethers of sugars or polyalcohols. These compounds are known under the term carbomer (Pharmeuropa vol. 8, No. 2, June 1996). Persons skilled in the art can also refer to U.S. Pat. No. 2,909,462 describing such acrylic polymers crosslinked with a polyhydroxylated compound having at least 3 hydroxyl groups, preferably not more than 8, the hydrogen atoms of at least three hydroxyls being replaced with unsaturated aliphatic radicals having at least 2 carbon atoms. The preferred radicals are those containing 2 to 4 carbon atoms, e.g. vinyls, allyls and other ethylenically unsaturated groups. The unsaturated radicals may themselves contain other substituents, such as methyl. The products sold under the name Carbopol® (BF Goodrich, Ohio, USA) are particularly appropriate. They are crosslinked with an allyl sucrose or with allylpentaerythritol. Among them, there may be mentioned Carbopol® 974P, 934P and 971P.

Among the copolymers of maleic anhydride and of alkenyl derivative, the EMA® copolymers (Monsanto) which are copolymers of maleic anhydride and of ethylene, which are linear or crosslinked, for example crosslinked with divinyl ether, are preferred. Reference may be made to J. Fields et al., Nature, 186: 778-780, Jun. 4, 1960.

The proportions of adjuvant which are useful are well known and readily available to the one skilled in the art. By way of example, the concentration of polymers of acrylic or methacrylic acid or of anhydride maleic and alkenyl copolymers in the final vaccine composition will be from 0.01% to 1.5% W/V, more particularly from 0.05 to 1% W/V, preferably from 0.1 to 0.4% W/V.

Further, leptospires are readily transmissible from one species to another when they cohabit the same area, making infection with several serovars possible. So various serovars of inactivated Leptospires may be present in multivalent immunogenic compositions and vaccine compositions.

The term immunogenic composition covers a composition which, once administered to the target species, induces an immune response directed against the Leptospires bacteria. The term vaccine is understood to mean a composition able to induce an effective protection. The target species are canines, bovines, porcines, equines, ovines, humans, preferably the dog, bitch, puppy, pig, piglet, sow, cattle, calf, beef, cow, horse, stallion, foal, mare, sheep, ewe, lamb.

Leptospiral serovars most frequently encountered in porcine, in bovine, in ovine, in equine and in canine are *canicola, icterohaemorrhagiae, grippotyphosa, pomona, hardjo, bratislava, ballum, aulumnalis* and *australis*.

The immunogenic compositions or vaccine compositions of the present invention may be carried out by the parenteral route, preferably by the subcutaneous route (SC), the intradermal route (ID), the intramuscular route (IM) or with a needleless injector.

The dose volumes of immunogenic compositions or vaccine compositions may be between 0.2 ml and 5 ml, preferably between 1 ml and 2 ml, containing from about 5.0 10e7 to about 5.0 10e9 bacteria/ml (per leptospiral serovar).

Advantageously, the immunogenic compositions or vaccine compositions of the present invention may be administered several times to the same animal without increasing the risk of adverse systemic vaccine reactions.

The invention will now be further described by way of the following non-limiting examples.

Example 1

Determination of the Maximum Growth Rate of Three Leptospires Strains

*Leptospira icterohaemorraghiae, Leptospira canicola* and *Leptospira grippotyphosa* were grown at 30° C. in several 14 ml glass test tubes filled with 10 ml semisolid modified JH medium (Johnson R. C. & Seiter C. W. (1977) "The *Leptospira* and their cultivation—a monograph", Reheis Chemical Company (a division of Armour Pharmaceutical), Phoenix, Ariz., USA, page 8).

The semisolid modified JH medium comprises: Na2HPO4 0.9 g/l, KH2PO4 0.27 g/l, NaCl 0.9 g/l, NH4Cl 0.225 g/l, glycerol 0.113 g/l, CaCl2 0.01 g/l, MgCl2 0.01 g/l, ZnSO4 0.004 g/l, FeSO4 0.05 g/l, CuSO4 0.0003 g/l, cyanocobalamin (B12 vitamin) 0.0002 g/l, HCl thiamine (B1 vitamin) 0.0045 g/l, agar 2.0 g/l, bovine albumin factor V 10 g/l, Tween® 80 2.5 g/l.

After from 4 to 10 days of incubation at 30° C., a disc of dense growth was obtained close to the surface of the culture medium in each test tube. Discs of dense growth are described in Czekalowski et al., British J. Exp. Pathol., 1953, 34, 588-595.

For each stain, two discs of dense growth were taken with a pipette and inoculated into a two liters Erlenmeyer containing 300 ml of liquid modified JH medium (Johnson R. C. & Seiter C. W. (1977) "The *Leptospira* and their cultivation—a monograph", Reheis Chemical Company (a division of Armour Pharmaceutical), Phoenix, Ariz., USA, page 8).

The liquid modified JH medium comprises: Na2HPO4 0.9 g/l, KH2PO4 0.27 g/l, NaCl 0.9 g/l, NH4Cl 0.225 g/l, glycerol 0.113 g/l, CaCl2 0.01 g/l, MgCl2 0.01 g/l, ZnSO4 0.004 g/l, FeSO4 0.05 g/l, CuSO4 0.0003 g/l, cyanocobalamin (B12 vitamin) 0.0002 g/l, HCl thiamine (B1 vitamin) 0.0045 g/l, bovine albumin factor V 10 g/l, Tween® 80 2.5 g/l.

These Erlenmeyers were incubated at 30° C. with shaking at 80 rpm (rotation per minute) in an orbital shaker during from 4 to 6 days.

During the culture, aliquots of Leptospires suspension were frequently taken for bacterial concentration determination.

The bacterial concentration was determined.

When the bacterial concentration had reached 0.8 10e9 bacteria/ml, each leptospire strain inoculum was transferred into a batch fermenter.

Prior to medium introduction, three 7 liters total volume batch fermenters were sterilized by heat. Three liters of sterile JH medium were transferred into these batch fermenters. 200 to 300 ml of one leptospire strain inoculum were introduced into a batch fermenter. For each batch fermenter, the pH value, the temperature and the dissolved oxygen value were followed. The pH value was adjusted to and maintained automatically at 7.2 by addition of sterile NH3 solution 7% (w/v). The temperature was adjusted to and maintained at 30° C. The dissolved oxygen value was maintained at 50% saturation by addition of pure oxygen gas in the medium through a sparger. Agitation and mixing was obtained by a Rushton turbine at 180 rpm.

After 80 to 100 hours, the culture was ended when the oxygen control stopped. During culture, aliquots were taken daily. Bacterial concentration was determined. The growth rate of each leptospire strain culture was then determined by the following formula:

Growth rate=[ln(concentration at time2)/ln(concentration at time1)]/(time2−time1)

The "time" corresponds to the time of culture starting from the inoculation, expressed in hours.

The maximum growth rate was the best growth rate obtained for each leptospire strain culture.

For *Leptospira icterohaemorraghiae* and *Leptospira canicola*, the maximum growth rate was about 0.045 h−1. For *Leptospira grippotyphosa*, the maximum growth rate was 0.06 h−1.

Example 2

Fed-Batch Cultures of *Leptospira icterohaemorraghiae, Leptospira canicola* and *Leptospira grippotyphosa*

*Leptospira icterohaemorraghiae, Leptospira canicola* and *Leptospira grippotyphosa*, obtained as described in example 1, were inoculated into one of the 3 Erlenmeyer containing 350 ml of liquid modified JH medium (example 1), respectively. The concentration of albumin in the JH medium depends on the nature of the strain: 10 g/l for *Leptospira icterohaemorraghiae,* 1 g/l for *Leptospira canicola* and 1 g/l for *Leptospira grippotyphosa.*

These Erlenmeyers were incubated at 30° C. with shaking at 80 rpm in an orbital shaker during from 4 to 6 days. During the culture, aliquots of Leptospires suspension were frequently taken for bacterial concentration determination.

When the bacterial concentration reached 0.8 10e9 bacteria/ml, each leptospire strain inoculum was transferred into one of the three fed-batch fermenters, previously sterilized by heat and containing 3 liters of sterilely JH medium without albumin and without Tween®.

The JH medium without albumin and without Tween® comprises: Na2HPO4 0.9 g/l, KH2PO4 0.27 g/l, NaCl 0.9 g/l, NH4Cl 0.225 g/l, glycerol 0.113 g/l, CaCl2 0.01 g/l, MgCl2 0.01 g/l, ZnSO4 0.004 g/l, FeSO4 0.05 g/l, CuSO4 0.0003 g/l, cyanocobalamin (B12 vitamin) 0.0002 g/l, HCl thiamine (B1 vitamin) 0.0045 g/l. The volume of inoculum depends on the nature of the strain: 150 ml for *Leptospira icterohaemorraghiae,* 300 ml for *Leptospira canicola* and 300 ml for *Leptospira grippotyphosa.*

For each fed-batch fermenter, the pH value, the temperature and the dissolved oxygen value were followed.

The pH value was adjusted to and maintained automatically at 7.2 by addition of sterile NH3 solution 7% (w/v). The temperature was adjusted to and maintained at 30° C. The dissolved oxygen value was maintained at 50% saturation by addition of pure oxygen gas in the medium through a sparger. Agitation and mixing was obtained by a Rushton turbine at 180 rpm.

1.8 liters of a 10 g/l Tween® 80 solution was prepared as a nutrient solution in a bottle equipped with a tube and a variable speed peristaltic pump for its feeding. Immediately after inoculation, the feeding started. The feed rate evolution in time was set in such a way that the specific growth rate of each leptospire strain was constant and below the maximum growth rates determined in example 1.

For all leptospire strains, this constant specific growth rate was equal to 0.03 h−1. In such conditions, the limiting factor for Leptospires growth in this culture is the Tween® 80.

The relationship between the Tween® 80 feed rate and specific growth rate is explained in detail in "The relationship between the nutrient feed rate and specific growth rate in fed batch cultures", R. C. Jones and R. M. Anthony, European J. Appl. Microbiol, 1977, 4, 87-92, particularly in page 88, chapter 1 "Constant specific growth rate".

The feed rate profile is calculated from this article with the following assumptions:

Tween® is the growth-limiting nutrient;

Kv is disclosed in this article equal to the cell weight at zero time divided by the product of the yield coefficient and the concentration of the growth limiting nutrient in the feed.

To simplify, we assumed that Kv is equal to the mass of Tween® initially present into the inoculum introduced into the culture medium divided by the concentration of the growth-limiting nutrient in the feed.

In the present example, 150 ml of *Leptospira icterohaemorraghiae* inoculum contains 0.150×2.5 g/l Tween®=0.375 g of Tween®; given that the Tween® solution is at 10 g/l concentration. Kv is then 0.0375 liter.

The fermentation was stopped when about 1.1 to 2 liters of the Tween® 80 nutrient solution were fed.

The results of each leptospire fed-batch culture are given in the following table.

TABLE 1 fed-batch cultures results

| | *Leptospira icterohaemorraghiae* | *Leptospira* canicola | *Leptospira grippotyphosa* |
|---|---|---|---|
| Final biomass concentration, bacteria/ml | 6.0 10e8 | 7.0 10e8 | 22.0 10e8 |
| Culture time | 112 hours | 110 hours | 120 hours |
| Volume of Tween ® solution fed | 1.1 liter | 1.4 liter | 2.0 liters |

These final biomass concentrations are in the range of what are usually obtained in one classical Leptospires batch culture. Another advantage is that no detoxifying agent was added and/or no treatment of the Tween® 80 was done, in contrario to the literature, where Tween® are detoxified, e.g. charcoal-treated, PVP-treated . . . .

Example 3

Adaptation of *Leptospira canicola* by Fed-Batch and Culture in a Protein-Free Medium 0.5 ml of a *Leptospira canicola* frozen bank was thaw and introduced into 100 ml of liquid modified JH medium (example 1) in a 500 ml Erlenmeyer. After incubation at 30° C. with shaking at 80 rpm in an orbital shaker for 6 days, the bacterial concentration reached 1.2 10e9 bacteria/ml; this pre inoculum culture 1 was transferred into another pre inoculum culture.

1.67 ml of the pre inoculum culture 1 were introduced into 100 ml of liquid modified JH medium in a 500 ml Erlenmeyer. After incubation at 30° C. with shaking at 80 rpm in an orbital shaker for 8 days, the bacterial concentration reached 1.6 10e9 bacteria/ml; this pre inoculum culture 2 was transferred into the inoculum culture.

9.37 ml of the pre inoculum culture 2 were introduced into 250 ml of liquid modified JH medium containing 3 g/l albumin in a two liters Erlenmeyer. After incubation at 30° C. with shaking at 80 rpm in an orbital shaker for 6 days, the bacterial concentration reached 7.5 10e8 bacteria/ml; the inoculum was transferred into the fed-batch fermenter.

Three liters of sterile JH medium without albumin and without Tween® (example 2) were prepared in a separate vessel and transferred to the fermenter.

150 ml of the *Leptospira canicola* inoculum culture were transferred into the medium.

The pH was adjusted to and maintained automatically at 7.2 by addition of sterile NH3 solution 7% (w/v). The temperature was adjusted to and maintained at 30° C. The dissolved oxygen was maintained at 50% saturation by addition of pure oxygen gas in the medium threw a sparger. Agitation and mixing is obtained by a Rushton turbine ran at 180 revolutions per minute (RPM).

1.8 liter of a 10 g/l Tween® solution was prepared as a nutrient solution in a bottle equipped with a tube compatible with a variable speed peristaltic pump for its feeding. Immediately after inoculation of the fermenter, the feeding was started. The feed rate evolution with time was set in such a way that the specific growth rate of the bacterial population was constant and below the maximum growth rate determined in example 1. This specific growth rate was equal to 0.025 $h^{-1}$.

When a bacterial concentration of 7.5 10e8 bacteria/ml was obtained, 10 ml of this *Leptospira canicola* suspension were inoculated in 100 ml of liquid JH medium without albumin in a 500 ml Erlenmeyer. This Erlenmeyer was incubated at 30° C. with shaking at 80 rpm in an orbital shaker up to 6 days. *Leptospira canicola* grew to 10.0 10e8 bacteria/ml.

Other passage cultures were done in the same way with JH medium without albumin with 1.25 or 2.5 g/l Tween® 80.

Similar growths and bacterial concentrations were obtained and observed since the eighth passage after the fed-batch culture. The higher growths and bacterial concentrations were obtained and observed for the eighth, sixth and fifth passage, with respectively 4.8 10e9, 2.1 10e9 and 3.2 10e9 bacteria/ml. Further passage is in culture.

Despite a culture process without a detoxifying agent, such as albumin, and with untreated Tween® 80, our final biomass concentrations are better than what is usually obtained in classical Leptospires batch cultures.

Example 4

Adaptation of Leptospires Strains to Grow in a Culture Medium without Albumin by Chemostat Culture Leptospires grow at 30° C. in several 14 ml glass test tubes filled with 10 ml semisolid modified JH medium (example 1). After 4 to 10 days of incubation, a disc of dense growth is visible close to the surface.

Two discs of dense growth are taken with a pipette and inoculated in 100 ml of liquid modified JH medium (example 1) contained in a 500 ml Erlenmeyer.

These Erlenmeyers are incubated at 30° C. with shaking at 80 rpm in an orbital shaker for 4 to 6 days. During the culture, aliquots of Leptospires suspension are frequently taken for bacterial concentration determination. When the bacterial concentration reaches 0.8 10e9 bacteria/ml, Leptospires inoculum is transferred into a chemostat. Prior to medium introduction, a chemostat is sterilized by heat. Half a liter of sterilely liquid modified JH medium (example 1) is prepared in a separate vessel and transferred into the chemostat through a filtration system for its sterilization.

100 ml of leptospire inoculum culture is introduced into the chemostat.

The pH is adjusted to and maintained automatically at 7.2 by addition of sterile NH3 solution 7% (w/v). The temperature is adjusted to and maintained at 30° C. The dissolved oxygen is maintained at 50% saturation by addition of pure oxygen gas in the medium threw a sparger. Agitation and mixing is obtained by a Rushton turbine ran at 180 rpm.

Five nutrient solutions are prepared. They contain Na2HPO4 0.9 g/l, KH2PO4 0.27 g/l, NaCl 0.9 g/l, NH4Cl 0.225 g/l, glycerol 0.113 g/l, CaCl2 0.01 g/l, MgCl2 0.01 g/l, ZnSO4 0.004 g/l, FeSO4 0.05 g/l, CuSO4 0.0003 g/l, cyanocobalamin (B12 vitamin) 0.0002 g/l, HCl thiamine (B1 vitamin) 0.0045 g/l, Tween® 80 1.25 g/l and various albumin concentrations: 10 g/l, 5 g/l, 2 g/l, 1 g/l, and no albumin, respectively.

These nutrient solutions are sterilely prepared in flasks equipped with a tube linked to a peristaltic pump.

After 4 to 6 days incubation, when the bacterial concentration reaches 0.8 10e9 bacteria/ml, the nutrient solution containing 10 g/l albumin is fed at a rate of 0.03 $h^{-1}$ (so below the maximum growth rate determined in example 1). For a culture volume of 500 ml, the fed rate is 15 ml/h.

During the chemostat culture, the weight of the culture is keeping constant by eliminating extra medium through another tube, equipped with a peristaltic pump, to a waste vessel.

When the equivalent of three volumes of the culture volume has been eliminated, the steady-state of the chemostat culture is obtained. At this moment, the 10 g/l albumin nutrient solution is replaced by the 5 g/l albumin nutrient solution. After another three volumes elimination, the nutrient solution is then replaced by the 2 g/l albumin nutrient solution, and so one till the nutrient solution containing 1 g/l and finally the nutrient solution containing no albumin at all.

When the equivalent of ten volumes of the culture has been eliminated again, the bacteria are adapted to grow in a medium containing traces of albumin and can be challenged to grow in a medium without albumin, in a batch mode.

Example 5

Production of a Leptospires Vaccine

One ml of a *Leptospira icterohaemorraghiae* frozen bank was thaw and introduced into 100 ml of liquid modified JH medium (example 1) contained in a 500 ml Erlenmeyer. After incubation at 30° C. with shaking at 80 rpm in an orbital shaker for 168 h the bacterial concentration reached 1.0 10e9 bacteria/ml; the pre inoculum was transferred into the inoculum culture.

30 ml of the pre inoculum culture were introduced into 300 ml of liquid modified JH medium contained in a two liters total volume Erlenmeyer. After incubation at 30° C. with shaking at 80 rpm in an orbital shaker for 120 h the bacterial concentration reached 2.4 10e9 bacteria/ml; 150 ml of the *Leptospira icterohaemorraghiae* inoculum was transferred into the fed-batch culture.

Prior to medium introduction, a 7 liters total volume fed-batch fermenter was sterilized by heat. Three liters of sterilely JH medium without albumin and without Tween® (example 2) were prepared in a separate vessel and transferred to the fermenter through a filtration system for its sterilization.

The pH was adjusted to and maintained automatically at 7.2 by addition of sterile NH3 solution 7% (w/v). The temperature was adjusted to and maintained at 30° C. The dissolved oxygen was maintained at 50% saturation by addition of pure oxygen gas in the medium threw a sparger. Agitation and mixing is obtained by a Rushton turbine ran at 180 rpm.

1.8 liter of a 10 g/l Tween® 80 solution was prepared as a nutrient solution in a bottle equipped with a tube linked to a variable speed peristaltic pump for its feeding. Immediately after inoculation of the fermenter, the feeding was started. The feed rate evolution with time was set in such a way that the specific growth rate of the bacterial population was constant and below the maximum growth rate determined in example 1. This specific growth rate was equal to 0.03 h−1.

The fermentation results are given in the following table.

TABLE 2

*Leptospira Icterohaemorraghiae* fed-batch culture results

| | *Leptospira icterohaemorraghiae* |
|---|---|
| Final Biomass concentration Bact/ml | 10.0 10e8 |
| Culture Time | 80 h |
| Volume of nutrient solution fed | 1.35 liter |
| Final volume | 4.5 liters |

The bacterial suspension was harvested. A first part of the bacterial suspension was inactivated with Thimerosal® (Sigma Chemical Co. St Louis, Mo. USA) at the concentration of 0.01% w/v at 30° C. for 24 hours. The second part of the bacterial suspension was inactivated with formaldehyde at a concentration of 0.02% w/v at 30° C. for 24 hours.

At the end of inactivation, the inactivated bacterial suspension was diluted by addition of physiologic water to obtain a final concentration of 6.0 10e8 bacteria/ml. A dose of vaccine contains 1 ml of this diluted inactivated bacterial suspension.

Example 6

Vaccination Study

The vaccine of example 5 was tested for efficacy at four dilutions in hamsters, followed by challenge.

41 hamsters, females, having a doby weight on day 0 from about 35 g to about 45 g were pooled into five groups (four "vaccinated groups" of 5 animals and one "control group" of 1 animal).

The two vaccines of example 5 were diluted by addition of a diluant (saline solution, pH 7.5) to obtain dilutions of 1/40, 1/160, 1/640 and 1/1280, respectively.

Each vaccinated groups of hamsters were vaccinated on day 0 with one of these four vaccine dilutions, sub-cutaneously with a dose of 1 ml.

All the hamsters, vaccinated and control, were challenged on day 15 with 200 LD50 (lethal dose 50) of a virulent *Leptospira icterohaemorragiae* strain.

Following challenge, the hamsters were daily observed during a 21-day period.

At the end of that period (day 36), the survival counts were used to measure vaccine efficacy.

TABLE 3

Vaccine efficacy results

| Groups | Vaccine dilution | Number of survivors |
|---|---|---|
| Thimerosal ® inactivated vaccinated group | 1/40 | 5 |
| | 1/160 | 5 |
| | 1/640 | 3 |
| | 1/1280 | 1 |
| Formaldehyde inactivated vaccinated group | 1/40 | 5 |
| | 1/160 | 4 |
| | 1/640 | 4 |
| | 1/1280 | 2 |
| Control group | — | 0 |

The no survival rate observed in the control group validates the challenge.

The survival rates observed in the vaccinated groups demonstrate the efficacy of the vaccine, with a dose-effect.

What is claimed:

1. A process for the culture of Leptospires in a protein-free culture medium wherein a fatty acid source is fed intermittently in such a way that the specific growth rate (μ) of Leptospires is less than its maximum growth rate (μmax) consisting essentially of:

(a) introducing the protein-free culture medium into a fed-batch fermenter, wherein the culture medium does not comprise any protein, polypeptide, peptide or detoxifying agent and is without any fatty acid source;

(b) inoculating the culture medium with a Leptospire strain;

(c) feeding into the culture medium a nutrient solution at a feed rate such that the specific growth rate (μ) is less than the maximum growth rate (μmax) of Leptospire strain, wherein the nutrient solution contains an untreated fatty acid which is fed into the medium to increase the concentration of untreated fatty acids to at least 1.25 g/l;

(d) continuing the culture until a substantial increase of the Leptospire biomass or at the end of the Leptospire growth; and (e) harvesting of the Leptospire biomass.

2. The process according to claim 1, wherein the specific growth rate (μ) is less than 0.045 $h^{-1}$.

3. The process according to claim 1, wherein the specific growth rate (μ) is less than 0.03 $h^{-1}$.

4. The process according to claim 1, wherein the specific growth rate (μ) is less than 0.025 $h^{-1}$.

* * * * *